United States Patent
Lacôme et al.

(10) Patent No.: US 6,537,336 B2
(45) Date of Patent: Mar. 25, 2003

(54) DIESEL FUEL COMPOSITIONS CONTAINING OXYGENATED COMPOUNDS DERIVED FROM TETRAHYDROFURFURYL

(75) Inventors: Thierry Lacôme, Garches (FR); Xavier Montagne, Rueil-Malmaison (FR); Bruno Delfort, Paris (FR); Fabrice Paille, Limay (FR)

(73) Assignee: Institut Français du Pétrole, Rueil-Malmaison (FR)

( * ) Notice: Subject to any disclaimer, the term of this patent is extended or adjusted under 35 U.S.C. 154(b) by 0 days.

(21) Appl. No.: 09/953,210

(22) Filed: Sep. 17, 2001

(65) Prior Publication Data

US 2002/0053161 A1 May 9, 2002

(30) Foreign Application Priority Data

Sep. 15, 2000 (FR) .............................. 00 11841

(51) Int. Cl.$^7$ .................................. C10L 1/18
(52) U.S. Cl. .............................. 44/350; 44/352; 44/447
(58) Field of Search .................. 44/350, 352, 447; 549/472, 429

(56) References Cited

U.S. PATENT DOCUMENTS

| | | | |
|---|---|---|---|
| 2,153,135 A | 4/1939 | Dickey et al. | |
| 2,535,012 A | 12/1950 | Croxall et al. | |
| 2,599,338 A | 6/1952 | Lifson et al. | |
| 3,072,607 A | 1/1963 | Fisch et al. | |
| 3,328,334 A | 6/1967 | Fuchsman | |
| 4,072,027 A | 2/1978 | Berenbaum et al. | |
| 4,891,049 A | 1/1990 | Dillon et al. | |
| 5,925,152 A | * 7/1999 | Barratt ........................ 44/350 |

FOREIGN PATENT DOCUMENTS

| | | |
|---|---|---|
| GB | 1539287 | 1/1979 |
| WO | 96/40844 | 12/1996 |
| WO | 99/66009 | 12/1999 |
| WO | 01/18155 | 3/2001 |

OTHER PUBLICATIONS

Yamashita, Junichi, Studies on Antitumor agents Chem. Pharm. Bull. 1987 35(6), 2373–81.*
Cornelis, Andre, Clay–supported Reagents; II Inst. Chim. Org. Biochim. Univ. Liege, Liege Synthesis 1982(2) 162–63.*

* cited by examiner

Primary Examiner—Cephia D. Toomer
(74) Attorney, Agent, or Firm—Millen, White, Zelano & Branigan, P.C.

(57) ABSTRACT

Diesel fuel compositions containing oxygenated compounds derived from tetrahydrofurfuryl having to the general formula:

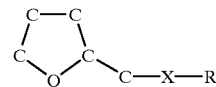

in which —X— is chosen from:
—O— and —O—[CH$_2$—O]$_n$— with n comprised between 1 and 20
and —R is chosen from:
alkyl groups containing from 1 to 30 carbon atoms; and
groups containing a tetrahydrofurfuryl unit.

9 Claims, No Drawings

DIESEL FUEL COMPOSITIONS CONTAINING OXYGENATED COMPOUNDS DERIVED FROM TETRAHYDROFURFURYL

FIELD OF THE INVENTION

The invention relates to diesel fuel compositions containing oxygenated compounds derived from tetrahydrofurfuryl. It also relates to new oxygenated compounds derived from tetrahydrofurfuryl.

BACKGROUND OF THE INVENTION

Today, the improvement of air quality is an absolute priority in all the large industrialized countries. Among the referenced emitters of pollutants, transport occupies a place that requires considerable measures to be taken to reduce its contribution. It is because of this that successive regulatory measures appeared several years ago, with new restrictions from the year 2000, in particular specifications on fuel quality. In fact, besides the characteristics conventionally specified, new regulations on the chemical composition of fuels have appeared, with the aim of limiting the precursors of some pollutants, such as particles, and compounds which react with tropospheric ozone or toxic compounds. In this context, it is obvious that all attempts aiming to improve the quality of products in order to offer mixtures that significantly reduce polluting emissions are promising.

SUMMARY OF THE INVENTION

It is one of the objects of the invention to propose the use of oxygenated compounds derived from tetrahydrofurfuryl as additives or formulation bases of gas-oils and leading to a significant lowering of particle emissions.

DETAILED DESCRIPTION OF THE INVENTION

The oxygenated compounds used in the diesel fuels according to the invention have the general formula:

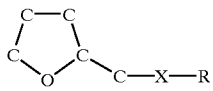

in which —X— is chosen from:
—O— and —O—[CH$_2$—O]$_n$— with n comprised of between 1 and 20
and —R is chosen from:
the alkyl groups containing from 1 to 30 carbon atoms, amongst which for example are the isopropyl, isobutyl, tertbutyl and tertamyl groups; and
the groups containing a tetrahydrofurfuryl unit, for example

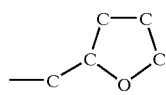

Among the preferred compounds for use in the diesel fuel compositions according to the invention, the following can be mentioned:
tetrahydrofurfuryl tertbutyl ether (I); and
acetal or a ditetrahydrofurfuryl polyacetal (II).

Their respective formulae are given below:

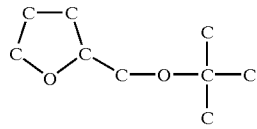

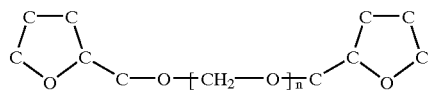

with n comprised between 1 and 20.

The different synthesis routes for these preferred compounds are described below.

Tetrahydrofurfuryl tertbutyl ether (I) can be prepared for example:
by reacting tetrahydrofurfuryl alcohol with for example a tertbutyl halide according to a standard esterification process, for example using Williamson's reaction; or
by adding tetrahydrofurfuryl alcohol to isobutene preferably using an acid catalyst chosen for example from sulfuric acid, sulphonic alkylbenzene acids and sulphonated polystyrene resins, such as Amberlyst 15® resin. It is the synthesis method that will be described in more detail in Example 1.

Ditetrahydrofurfuryl acetal and polyacetals (II) are generally produced from the reaction of tetrahydrofurfuryl alcohol with formaldehyde, either in its monomer form, or in its polymer form called paraformaldehyde of (CH$_2$O)x structure, or in its cyclic trimer form called trioxane, of formula:

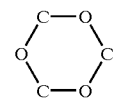

It is this latter synthesis route which is illustrated in Example 2.

This reaction is in general catalyzed by acids such as for example sulfuric acid, sulphonic resins such as Amberlyst 15® resin or the Lewis acids.

These products can also be prepared by exchange reaction between tetrahydrofurfuryl acid and an acetal such as for example dimethoxymethane, also called methylal.

In the fuel compositions for diesel engines according to the invention, the oxygenated compounds derived from tetrahydrofurfruyl can be used in low concentrations, as additives, in standard diesel fuels of petroleum origin (middle distillates of petroleum), optionally containing in varying proportions, other oxygenated compounds such as alkyl esters derived from vegetable oils. They can also be used as additives. The concentration of oxygenated compounds according to the invention can thus be for example from 0.01 to 1%, preferably from 0.05 to 0.2% by weight.

The oxygenated compounds derived from tetrahydrofurfuryl can also be used as basic constituents of diesel fuel. In this use, they can represent for example up to 40% and preferably up to 30% by weight of the fuel.

More usual proportions of oxygenated compounds derived from tetrahydrofurfuryl are in the region of 10 to 15% by weight.

In all of the cases mentioned above the fuels for diesel engines according to the invention can still contain all the other conventional additives, in the usual concentrations.

According to the invention, the fuels described above can supply all types of diesel engines, with direct or indirect fuel injection.

The invention also provides new oxygenated compounds of tetrahydrofurfuryl, namely ditetrahydrofurfuryl polyacetals of formula (II) with n greater than 1.

The following examples illustrate the invention without limiting it.

EXAMPLES

In Examples 1 and 2, the synthesis of compounds (I) and (II) is described.

Example 1

Synthesis of Tetrahydrofurfuryl Tertbutyl Ether (I)

The reaction implemented is the following:

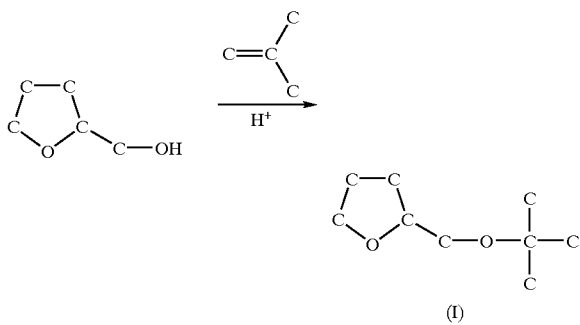

(I)

102 g (1 mole) of tetrahydrofufuryl alcohol and 0.3 g of Amberlyst 15® resin are introduced into a pressure resistant reaction vessel. The reaction vessel is heated so as to maintain the reaction medium at 50° C., then isobutene is introduced in such a way as to add 68 g (1.21 mol) over 4 hours. After returning the reaction medium to ambient temperature, separation of the catalyst by filtration is carried out, then elimination by evaporation under reduced pressure at ambient temperature of the residual dissolved isobutene and possible by-products. 151 g of a colorless liquid is collected, the analysis of which conforms to the structure of the desired product.

After returning the reaction medium to ambient temperature, neutralization of the medium is carried out using 200 ml of a 0.1M hydrochloric acid solution in alcohol. After filtration of the salt formed and evaporation under reduced pressure of the alcohol, 150 g of a liquid is collected, the analysis of which conforms to the desired ditetrahydrofurfuryl carbonate structure.

Analysis by infra-red spectroscopy indicates the presence of a signal at 1740 cm$^{-1}$ characteristic of the carbonate function and the absence of a signal at 3300 cm$^{-1}$ characteristic of the hydroxyl group present in the starting tetrahydrofurfuryl alcohol.

Example 2

Synthesis of the Ditetrahydrofurfuryl Acetal (II)

The reaction implemented is the following:

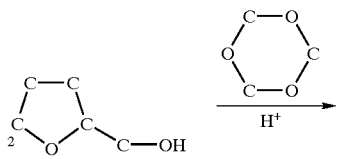

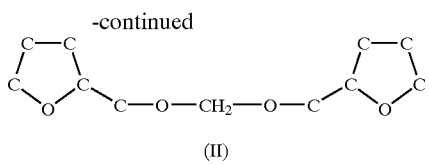

(II)

102 g (1 mole) of tetrahydrofurfuryl alcohol, 9 g (0.1 mole) of trioxane and 0.25 g of Amberlyst 15® resin is introduced into a closed metallic reaction vessel equipped with a stirrer. The mixture is heated at 50° C. for 2 hours, then at 90° C. for 1 hour. After returning to ambient temperature, the medium is diluted with 250 ml of toluene, followed by elimination of the catalyst by filtration, and then the excess reagents are evaporated off under reduced pressure. 55 g of a clear liquid is obtained, the analysis of which conforms to the structure of the desired product.

Example 3

Tests have been carried out with the aim of evaluating the impact of incorporating oxygenated compounds (I) and (II), for an incorporation rate of 10% by weight, corresponding to an incorporation of oxygen of up to 5% by weight, in the polluting emissions of a diesel engine. By way of comparison tetrahydrofurfuryl alcohol was tested.

The oxygenated compounds used are noted as follows:
tetrahydrofurfuryl alcohol: THFA:
tetrahydrofurfuryl tertbutyl ether (I): THFA/TBE:
ditetrahydrofurfuryl acetal (II): THFA/acetal.

The tests were carried out on a diesel vehicle equipped with a direct fuel injection engine.

These tests were carried out on the cycle imposed by directive 70/220/CE, modified by directive 98/69/EC (cycle called MVEG-11s Euro 2000). This cycle is composed of an urban phase (ECE cycle with a length of 4.052 km) and an extra-urban phase (EUDC cycle with a length of 6.955 km). The results of tests, presented in g/km, are expressed in terms of efficiency on each of the phases of the cycle and the complete cycle.

The tests were carried out starting with a gas-oil representative of Euro 2000 formulations (density of the order of 835 at 15° C., sulfur content of the order of 300 ppm, cetane index in the order of 53, distillation range 170/366° C.).

The results obtained are presented in the following tables:

|  | Reference gas-oil | THFA (comp.) | THFA/TBE | THFA/acetal |
| --- | --- | --- | --- | --- |
| Results on MVEG cycle (g/km) | | | | |
| Particles | 0.07198 | 0.0585 | 0.05915 | 0.0575 |
| Results on ECE cycle (g/km) | | | | |
| Particles | 0.0603 | 0.0442 | 0.04865 | 0.04568 |
| Results on EUDC cycle (g/km) | | | | |
| Particles | 0.0788 | 0.0669 | 0.0653 | 0.0584 |

The use according to the invention of the range of oxygenated compounds derived from tetrahydrofurfuryl leads to a reduction in particle emissions of the order of 30% under all of the test conditions.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 00/11841, filed Sep. 15, 2000, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A composition of diesel fuel comprising at least one oxygenated compound derived from tetrahydrofurfuryl and having the general formula:

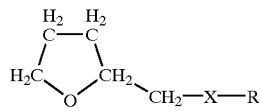

in which —X— is —O— or —O—[$CH_2$—O]$_n$—, wherein n is from 1 to 20, and —R is an alkyl group containing about 1 to 30 carbon atoms or a group containing a tetrahydrofurfuryl unit.

2. A diesel fuel composition according to claim 1 wherein, in the general formula of the oxygenated compound, —R is selected from the group consisting of isopropyl, isobutyl, tertbutyl and tertamyl groups.

3. A diesel fuel composition according to claim 1 wherein, in the general formula of the oxygenated compound, —R is a tetrahydrofurfuryl unit of the formula:

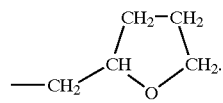

4. A diesel fuel composition according to claim 1, wherein said oxygenated compound derived from tetrahydrofurfuryl, used as an additive, is present, in the composition in a concentration of from 0.01 to 1% by weight.

5. A diesel fuel composition according to claim 1, wherein said oxygenated compound derived from tetrahydrofurfuryl, used as an additive, is present, in the composition in a concentration of from 0.05 to 0.2% by weight.

6. A diesel fuel composition according to claim 1, wherein said oxygenated compound derived from tetrahydrofurfuryl, used as a basic constituent, is present in a concentration of 10–40% by weight.

7. A diesel fuel composition according to claim 1, wherein said oxygenated compound derived from tetrahydrofurfuryl, used as a basic constituent, is present in a concentration of 10–30% by weight.

8. A diesel fuel composition according to claim 1, wherein said oxygenated compound derived from tetrahydrofurfuryl, used as a basic constituent, is present in a concentration of 10–15% by weight.

9. A diesel fuel composition according to claim 1, wherein the diesel fuel is chosen from diesel fuels of petroleum origin and alkyl ester mixtures derived from vegetable oils.

* * * * *